United States Patent [19]

Deniega et al.

[11] Patent Number: 5,649,903
[45] Date of Patent: Jul. 22, 1997

[54] APPARATUS AND METHODS FOR GENERATING LEUKOCYTE FREE PLATELET CONCENTRATE

[75] Inventors: Jose C. Deniega, Lake Forest; Daniel H. Duff, Irvine; Donald W. Schoendorfer; William R. Miller, both of Santa Ana, all of Calif.

[73] Assignee: Baxter International Inc., Deerfield, Ill.

[21] Appl. No.: 373,359

[22] Filed: Jan. 17, 1995

Related U.S. Application Data

[62] Division of Ser. No. 890,980, May 29, 1992, Pat. No. 5,403,272.

[51] Int. Cl.⁶ .................................................. A61M 37/00
[52] U.S. Cl. ......................................................... 604/4; 604/6
[58] Field of Search .................... 604/4–6; 210/321.67, 210/321.68, 321.87, 651

[56] References Cited

U.S. PATENT DOCUMENTS

| | | | |
|---|---|---|---|
| 4,944,883 | 7/1990 | Schoendorfer | 240/782 |
| 4,985,153 | 1/1991 | Kuroda et al. | 210/782 |
| 5,034,135 | 7/1991 | Fischel | 210/782 |
| 5,298,165 | 3/1994 | Oka et al. | 210/645 |
| 5,403,272 | 4/1995 | Deniega et al. | 604/4 |

*Primary Examiner*—John G. Weiss
*Assistant Examiner*—David J. Cho
*Attorney, Agent, or Firm*—Stetina Brunda Buyan; Bruce Canter

[57] ABSTRACT

Methods and devices for separating leukocytes from a leukocyte contaminated blood fraction by use of a rotating membrane filter apparatus. The invention includes methods/devices for preparing substantially leukocyte free platelet concentrate for therapeutic use. The devices of the invention include a rotating membrane filter apparatus for leukocyte separation as well as tubing harness/component systems (FIGS. 2a, 2b, 2c) useable in connection with automated apheresis instruments.

13 Claims, 7 Drawing Sheets

STAGE 2

FILTRATE OUT

APPARATUS AND METHODS FOR GENERATING LEUKOCYTE FREE PLATELET CONCENTRATE

RELATED CASES

This application is a divisional of U.S. application Ser. No. 07/890,980, now U.S. Pat. No. 5,403,272, filed on May 29, 1992.

FIELD OF THE INVENTION

The present invention relates generally to medical apparatus and methods and, more particularly, to apparatus and methods for obtaining substantially leukocyte free platelet concentrate from whole blood.

BACKGROUND OF THE INVENTION

In medical practice it is sometimes desirable to transfuse patients with quantities of platelet concentrate as a means for treating thrombocytopenia and/or subnormal thrombocyte counts as may result from various systemic disorders or following certain medical procedures. Typically, such platelet transfusions are administered in the form of a platelet-plasma concentrate containing approximately 1.5–1.8 million platelets per microliter of plasma. Such platelet concentrate is typically packaged and utilized in "units" each unit having a volume of 200 milliliters.

Platelet concentrates for transfusion have heretofore typically been prepared by first extracting platelet-rich plasma from whole blood, and subsequently subjecting the platelet-rich plasma to a secondary concentration process whereby additional plasma is removed so as to leave the desired platelet concentration of 1.5–1.8 million platelets per microliter. One example of an automated method/device for obtaining platelet concentrate from whole blood is described in Schoendorfer, D. W., Williamson, L. H., Sheckler, V. L. and Fitzgerald, B. P.: Platelet Collection with the Autopheresis-C® Apheresis System; Vox Sanguinis, 58: 100–105 (1990).

The instrumentation and methodology heretofore utilized to obtain platelet concentrate generally allows quantities of contaminating leukocytes to remain in the final platelet concentrate. By some processes, the level of contaminating leukocytes contained in the platelet concentrate may be in the range of $10^6$–$10^9$ leukocytes per 200 ml unit of platelet concentrate.

The presence of leukocytes within the platelet concentrate is undesirable because leukocytes are much more immunogenic than platelets. The presence of contaminating leukocytes in platelet concentrate infusions may have been associated with various responses that are detrimental to the recipient of the transfusion. Such responses may include pyrogenic febrile reactions, refractoriness to platelet transfusions due to alloimmunization to HLA antigens found on the surfaces of the leukocytes and graft-host diseases caused by transfusion of lymphocytes into immunodeficient patients. Also, the presence of contaminating leukocytes may result in transmission of leukocyte-associated vital diseases, many of which may cause severe illness or even death.

In view of the adverse effects associated with the presence of leukocytes in platelet transfusions, it is desirable to devise methods for removing or excluding some or all of the contaminating leukocytes from the platelet concentrate.

Centrifugation has been explored as one possible means of removing unwanted leukocytes from platelet concentrate. However, centrifugation techniques are less than optimal for this purpose due to indefiniteness of the interface formed between the resultant layers of leukocytes and platelets. Leukocyte removal filters utilized for this purpose have typically incorporated filtration material(s) capable of selectively adsorbing leukocytes from the platelet concentrate, based on differences in the surface properties of the leukocytes and platelets. At least one commercially available leukocyte removal filter incorporates a matrix of non-woven polyester fibers over which the leukocyte contaminated platelet concentrate is gravity fed. (Sepacell®, Asahi Medical Co., Ltd., Tokyo, Japan) Removal of leukocytes from platelet concentrate by the use of such adsorption filters may be problematic due to some populations of leukocytes having non-typical surface characteristics not attracted by the filter material and/or frequent exhaustion or diminution in efficiency of the filter due to occupation of the filter surfaces by adsorbed leukocytes.

In view of the shortcomings associated with the existing methods for removing leukocytes from platelet concentrate, there remains a need in the art for the development of new, improved and/or automated methods for extracting or removing some or all of the contaminating leukocytes found in collected platelet concentrates.

SUMMARY OF THE INVENTION

The present invention provides a method and device for removing platelets from a platelet contaminated blood fraction (eg leukocyte contaminated platelet-rich plasma or leukocyte contaminated platelet concentrate) through the use of a rotating membrane filter apparatus. The method/device of the present invention may be combined with prior art devices and methods to arrive at a three-stage process for obtaining substantially leukocyte free platelet concentrate from whole blood.

In accordance with the invention, there is provided a method of extracting leukocytes from a leukocyte contaminated blood fraction, said method comprising the passage of said leukocyte contaminated blood fraction through a rotating membrane filter having a multiplicity of pores formed therein. The pores of the rotating membrane filter are sufficiently large to permit passage therethrough of plasma and platelets but sufficiently small to prevent passage therethrough of leukocytes. The membrane filter is rotated during the filtration process to improve efficiency and prevent clogging of the membrane pores.

Further in accordance with the invention, there is provided a three-staged process for obtaining leukocyte depleted platelet concentrate (LDPC) from whole blood. The first stage of the process comprises the centrifugal separation of platelet-rich plasma from the whole blood. The second stage of the process comprises the extraction of a quantity of cell free plasma from the platelet-rich plasma obtained in Stage 1. Such results in the production of a leukocyte contaminated platelet concentrate (LCPC) having a desired concentration of platelets therein. Such second stage of the process may be accomplished by way of a rotating membrane filter apparatus having membrane pores sized less than 1 micron. The third stage of the process comprises the separation of leukocytes from the leukocyte contaminated platelet concentrate (LCPC) to yield a desired leukocyte depleted platelet concentrate (LDPC). Such third stage of the process may be carried out by a rotating membrane filter apparatus having membrane pores of approximately 3.0–3.5 microns in size.

Further in accordance with the invention, there is provided an alternate three-stage process for obtaining leukocyte depleted platelet concentrate (LDPC) from whole blood. The first stage of such alternate process comprises the centrifugal separation of leukocyte contaminated platelet-rich plasma from whole blood. The second stage of such alternate process comprises the removal of leukocytes from the leukocyte contaminated platelet-rich plasma generated in stage 1 to yield a leukocyte depleted platelet-rich plasma (LDPRP). Such removal of leukocytes from the leukocyte contaminated platelet-rich plasma may be effected by way of a rotating membrane filter apparatus having pores of approximately 3.0–3.5 microns formed therein. The third stage of such alternate process comprises the removal of a quantity of substantially cell free plasma from the leukocyte contaminated platelet-rich plasma (LCPRP) obtained in stage 2, thereby yielding a leukocyte depleted platelet concentrate (LDPC) having a desired concentration of platelets therein.

Further in accordance with the invention, there is provided a rotating membrane filter apparatus for removing leukocytes from a leukocyte contaminated blood fraction (eg leukocyte contaminated platelet-rich plasma or leukocyte contaminated platelet concentrate). Such rotating membrane separation apparatus comprises a rigid outer housing having a rotatable membrane filter element positioned therein. Inflow and outflow ports are formed in the housing to facilitate inflow of the platelet contaminated blood fraction thereinto and outflow of a) the filtered platelets and b) the leukocyte depleted blood fraction, therefrom. The rotating membrane filter element of the apparatus comprises a membrane having pores of approximately 3.0–3.5 microns in size formed therein. The rotatable membrane filter element is preferably rotatable at 1600–1800 r.p.m. The rigid outer housing of the apparatus is preferably sized, relative to the rotatable membrane filter element, such that an optimal gap width is formed therebetween for passage of the unfiltered material thereinto. Such optimal gap width is preferably 0.020–0.030 inches in width.

Still further in accordance with the invention, there are provided tubing component sets for use in connection with automated apheresis instruments to carry out the process of the present invention.

Further objects, advantages and elements of the invention will become apparent to those skilled in the art upon reading and understanding of the following detailed description and the accompanying drawings to which such detailed description refers.

BRIEF DESCRIPTION OF THE DRAWINGS

FIG. 3b is a longitudinal sectional view of the device of FIG. 3a.

FIG. 3c is a cross-sectional view through line 3c—3c of FIG. 3a.

FIG. 4b is a cross-sectional through line 4b—4b of FIG. 4a.

DETAILED DESCRIPTION OF PREFERRED EMBODIMENTS

The detailed description set forth below, and the showings set forth in the accompanying drawings, are intended merely to describe and illustrate certain presently preferred embodiments of the invention, and are not intended to represent the only form in which the present invention may be constructed or utilized. It is to be understood that the same or equivalent functions and sequences may be accomplished by different embodiments that are also within the spirit and scope of the present invention.

A. The Process of the Invention

Figure 1:
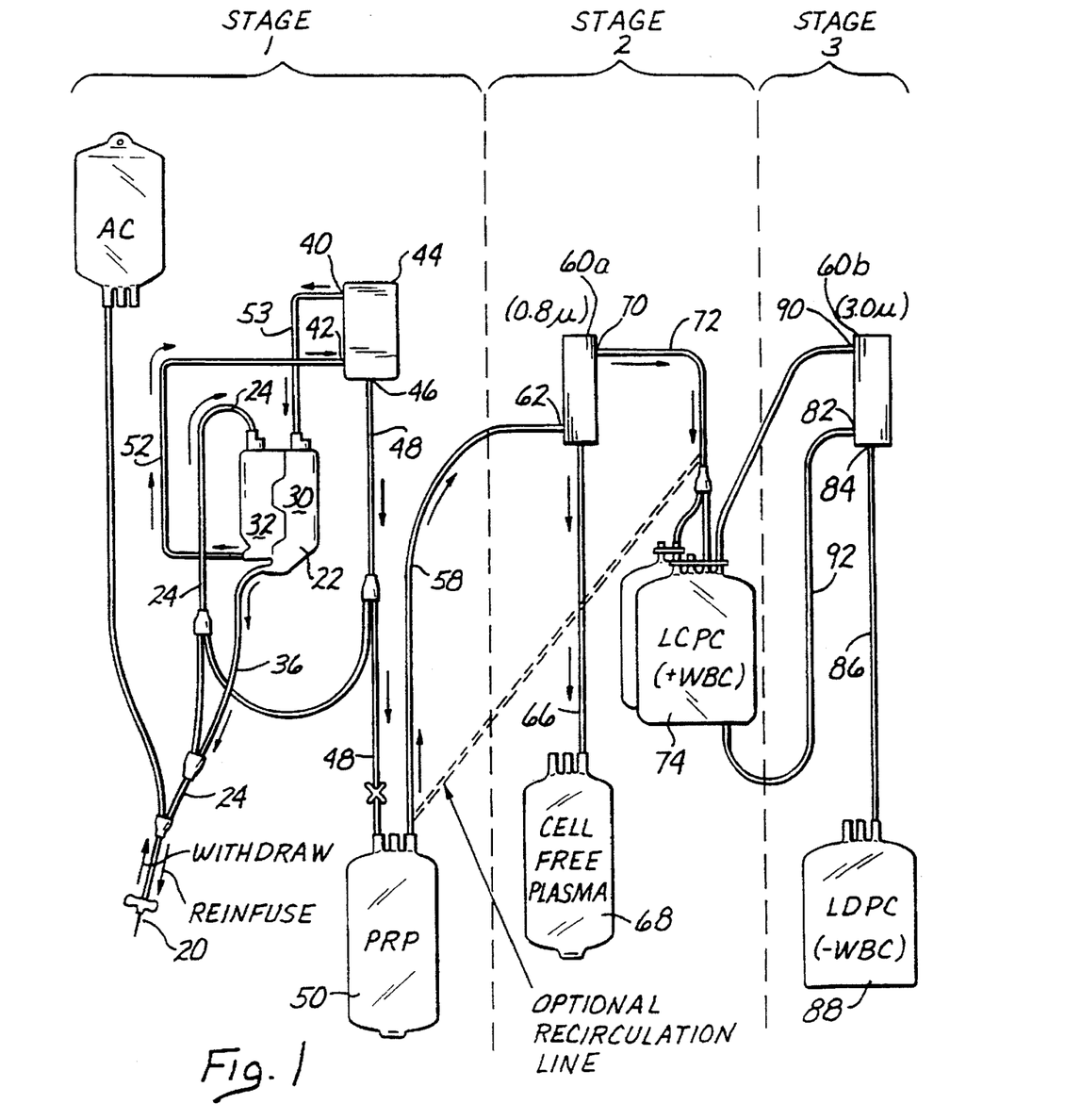
FIG. 1 is a schematic showing of the apparatus and method of the present invention.

Referring to FIG. 1, a preferred embodiment of the process of the present invention comprises three stages, as described more fully herebelow.

i. Stage 1 of the Process

Stage 1 of the process shown in FIG. 1 comprises the separation of platelet-rich plasma (PRP) from whole blood. In the embodiment shown in FIG. 1, a venipuncture needle 20 is inserted into an appropriate blood vessel and blood is withdrawn through venipuncture needle 20 and through blood tube 24 into the left chamber 32 of reservoir 22. An anticoagulant container 26 is attached to blood tube 24 by way of anticoagulant tube 28. A metering pump, specific drip rate, adjustable pressure exerting means or other metering device is utilized to deliver a metered amount of anticoagulant from anticoagulant container 26 into the blood being withdrawn through blood tube 24.

Reservoir 22 is divided into a pair of side by side compartments 30, 32. Whole blood is withdrawn into left chamber 32 of reservoir 22 through blood tube 24. Blood exits chamber 32 through tube member 52, and passes through tube 52 into the inlet port 42 of whole blood separator apparatus 44.

Whole blood separator apparatus 44 comprises a rotating centrifugal separator apparatus capable of separating whole blood into (a) a platelet-rich plasma fraction and (b) a cell concentrate fraction. A presently preferred whole blood separator apparatus 44a useable in the present invention is specifically shown in FIGS. 3a, 3b and 3c and is specifically described in detail herebelow.

Supernatant platelet-rich plasma (PRP) is separated from the remaining constituents of the whole blood and the PRP exits separator apparatus 44 through PRP outlet port 46 and passes through PRP tube 48 into PRP container 50.

Optionally, the color or hemoglobin content of the platelet-rich plasma (PRP) may be monitored or measured prior to entry into the PRP container 50 to discern the presence of red blood cells. If such optional monitoring of color or Hb content indicates an unacceptably high red cell content, the platelet rich plasma (PRP) may be diverted back into the left chamber 32 of reservoir 22 to undergo repeated separation.

The cell concentrate (CC) component of the whole blood exits separator apparatus 44 through cell concentrate outlet port 40 and passes through cell concentrate outlet tube 53 into the right chamber 30 of reservoir 22.

Withdrawal of whole blood through blood tube 24 is preferably cycled or periodically interrupted to permit cell concentrate which has become collected in the right chamber 30 to be periodically pumped or otherwise passed from the right chamber 30 of reservoir 22, through draw tube 36, through the distal portion of blood tube 24, and back into the patient's blood vessel through venipuncture needle 20.

The whole blood separation apparatus 44 of Stage 1 may comprise a rotating centrifugal separator capable of separating platelet-rich plasma (PRP) from whole blood. The term Platelet-Rich Plasma, as used in this specification, shall mean blood plasma having both platelets and white blood cells contained therein. Typically, the platelet-rich plasma (PRP) will contain platelets in the range of $4 \times 10^8$–$6 \times 10^8$/ml and leukocytes in the range of $2 \times 10^5$–$2 \times 10^6$/ml.

ii. Stage 2 of the Process

Figure 4A:
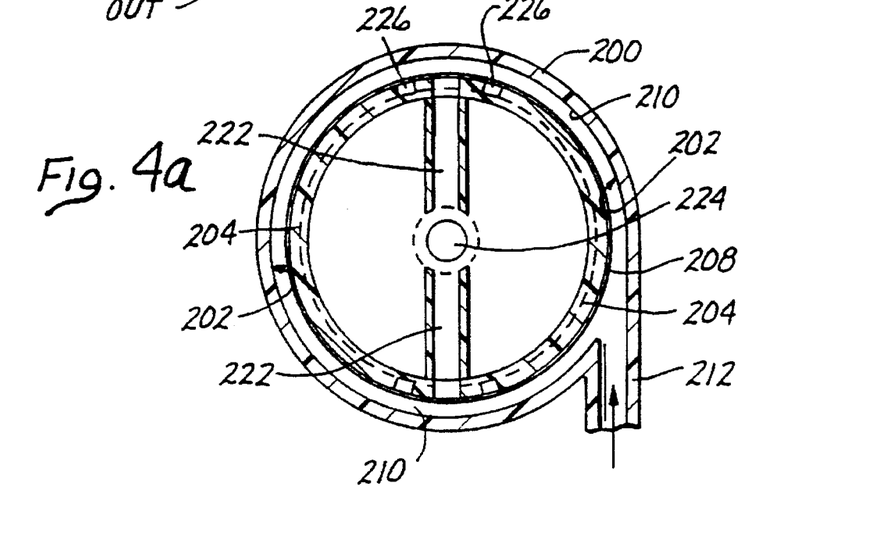
FIG. 4a is a cut-a-way perspective view of a rotating membrane filter device useable with a pore size membrane to prepare platelet concentrate from platelet-rich plasma in accordance with Stage 1 or 2 of the process of the present invention and also useable with a pore size membrane to prepare platelet concentrate in accordance with Stage 2 or 3 of the process of the present invention.
Figure 4B:
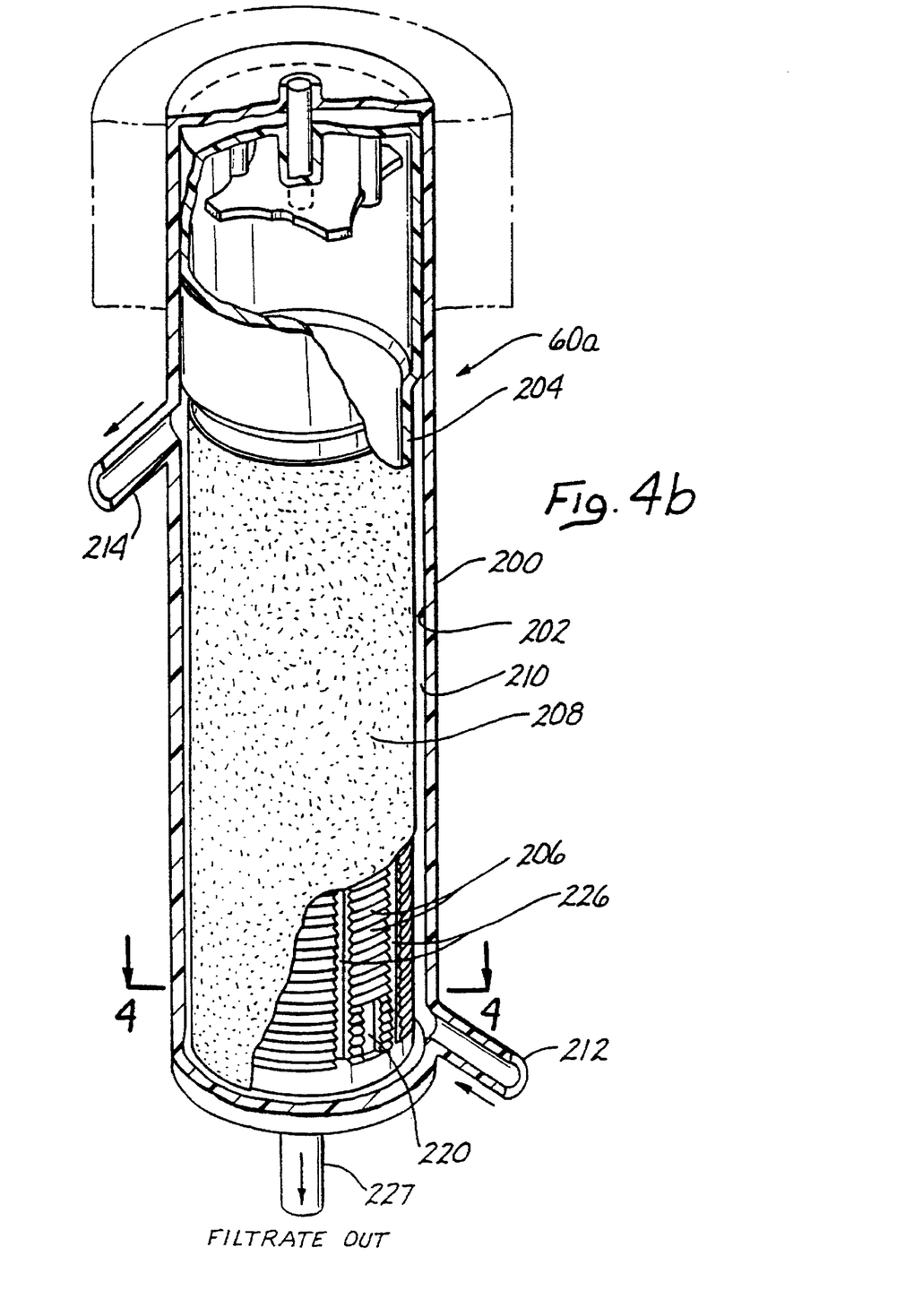

As shown in FIG. 1, during stage 2 of the process the platelet-rich plasma (PRP) collected in the platelet-rich plasma container 50 is subsequently pumped or otherwise withdrawn through platelet-rich plasma tube 58, through inlet port 62 and into platelet-rich plasma separator apparatus 60a. Platelet-rich plasma separator apparatus 60a may comprise any type of separator apparatus capable of separating platelet-rich plasma into (a) a platelet concentrate component and (b) a cell free plasma component. A presently preferred platelet-rich plasma separator apparatus 60 useable in conjunction with the present invention is shown in FIGS. 4a and 4b and described in detail herebelow. Cell free plasma exits the platelet-rich plasma separator 60a through cell free plasma outlet port 64 and passes through cell free plasma tube 66 into cell free plasma container 68. Platelet concentrate passes (PC) out of platelet-rich plasma separator apparatus 60a through platelet concentrate outlet port 70, through platelet concentrate tube 72 and into platelet concentrate container 74. Such platelet concentrate contains at least contaminating quantities of leukocytes which are subject to removal during Stage 3 of the process.

Optionally, as indicated by the dotted lines on FIG. 1, the leukocyte contaminated platelet concentrate exiting the separator apparatus 60a in Stage 2 of the process may flow from line 72 back into the platelet-rich plasma container 50 so as to provide for a recirculating process. In such recirculating process the leukocyte containing platelet concentrate will mix with any remaining platelet-rich plasma contained in container 50 and will be recirculated through separator apparatus 60a via line 58. Such recirculation will continue until the desired amount of cell free plasma has been collected in container 68 and/or until the mixture of platelet-rich plasma and leukocyte contaminated platelet concentrate contained within container 50 has reached a desired quantity.

iii. Stage 3 of the Process

In accordance with Stage 3 of the process, leukocyte contaminated platelet concentrate (LCPC) is pumped or otherwise withdrawn from platelet concentrate container 74 through platelet concentrate tube 92 and into a platelet concentrate/WBC separator apparatus 60b. Platelet concentrate/WBC separator apparatus 60b may comprise any separator apparatus capable of separating leukocytes from leukocyte contaminated platelet concentrate (LCPC) to yield a quantity of leukocyte depleted platelet concentrate (LDPC).

Leukocyte contaminated platelet concentrate (LCPC) is withdrawn through platelet concentrate tube 92 and into the platelet concentrate/WBC separator apparatus 60b through PC inlet port 82. Leukocyte depleted platelet concentrate (LCPC) exits the platelet concentrate/WBC separator apparatus 60b, through LCPC outlet port 84, passes through LDPC tube 86, and into LCPC container 88. The unfiltered plasma containing leukocytes exits the platelet concentrate/WBC separator apparatus 60b through recirculation outlet port 214. Such leukocyte containing unfiltered plasma then passes through return line 90 and, back into platelet concentrate container 74. Thus, the leukocyte containing unfiltered plasma is then recirculated through the PC/WBC separator apparatus 60b in the manner shown.

B. Preferred Devices of the Present Invention i. A Preferred Centrifugal Separator Apparatus
Useable in Stage 1

Figure 3A:
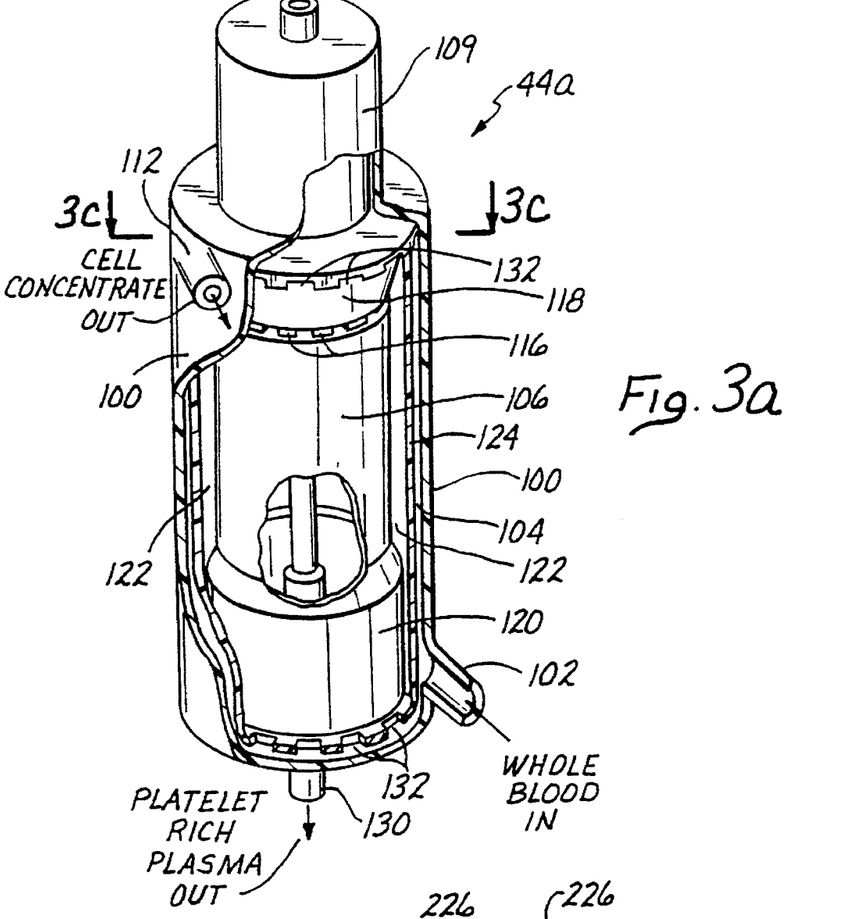
FIG. 3a is a cut-a-way perspective view of a rotating whole blood separation device separating platelet-rich plasma from whole blood in accordance with the process of the present invention.
Figures 3B, 3C:
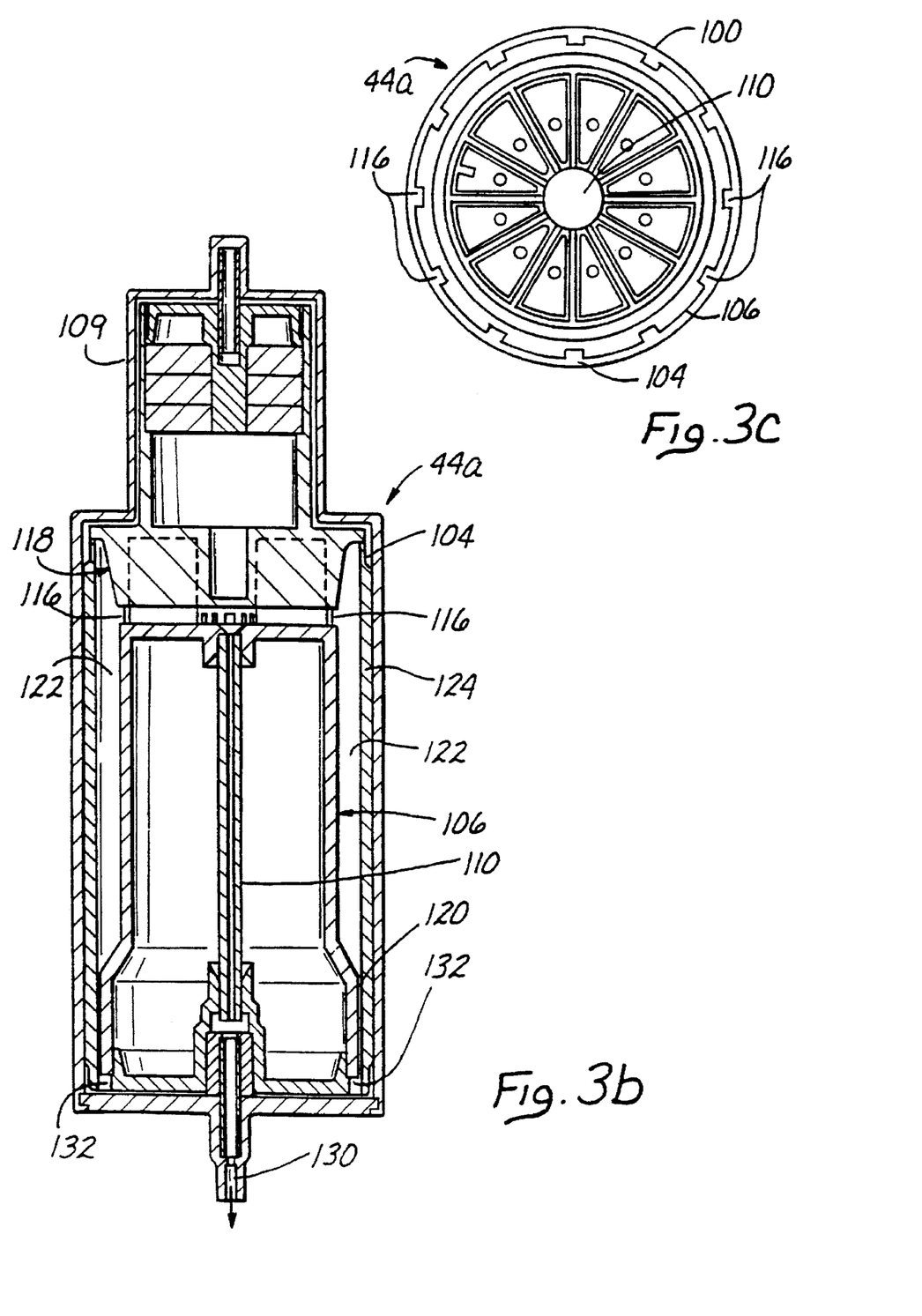

FIGS. 3a, 3b and 3c show a presently preferred whole blood separator apparatus 44a for separating whole blood into a) a platelet-rich plasma fraction and b) a cell concentrate fraction. The preferred whole blood separator apparatus 44a is fully described and shown in U.S. Pat. No. 4,944,883 (Schoendorfer, et al.) and available commercially under the name PLATELETCELL™ from Baxter Healthcare Corporation, Fenwal Division, Deerfield, Ill.

The entire disclosure of U.S. Pat. No. 4,944,883 (Schoendorfer, et al.) is expressly incorporated herein by reference as if completely set forth in its entirety in this application.

In summary, the preferred whole blood separator apparatus 44a comprises an outer housing or shell 100 of generally cylindrical configuration on a generally vertical axis. A whole blood inlet port 102 is formed near the bottom of housing 100 and comprises a tubular member positioned tangentially proximate the housing 100. A cell concentrate outlet port 112 is formed near the top end of housing 100 and comprises a hollow tubular member which extends tangentially to the housing 100.

A double walled rotor 108 is rotatably mounted within housing 100 and is connected, by way of rotatable shaft 110, to a magnetic drive unit 109 positioned at the top of the whole blood separator apparatus 44a. When subjected to a rotating magnetic field, the magnetic drive unit 109 rotationally drives rotor 108 at a desired rotational rate, preferably in the range 2,000–3,800 r.p.m. and most preferably at approximately 3,600 r.p.m.

The double walled rotor 108 spans the axial length between the blood inlet port 102 and the cell concentrate outlet port 112. Such double walled rotor 108 includes an inner cylindrical core 114 having a substantially continuous surface except for circumferentially disposed platelet concentrate ports 116 formed near its upper end. Above platelet concentrate ports 116 the rotor 108 includes an outwardly tapered or divergent wall portion 118. Similarly, at the bottom end of rotor 108 there is an outwardly tapered basal portion 120 of enlarged diameter. The upper portion 118, basal portion 120 and principal mid-portion 106 of rotor 108 form the inner core 114 of the rotor 108. The space 122 between the outer surface of the inner core 114 of rotor 108 and the outer wall 124 thereof forms a centrifugation zone within the rotor 108.

It is preferable that the platelet-rich plasma ports 116 formed in rotor 108 be of rectangular shape approximately 0.035 inches wide by 0.075 inches high.

A recirculation flow gap 104 exists between the outer surface of the rotor outer wall 124 and the inner surface of the cylindrical housing 100. In the preferred embodiment, such recirculation gap 104 is approximately 0.006 inches wide along the majority of its length. Such re-circulation flow gap 104 may be made wider at the upper and lower ends thereof, adjacent the whole blood inlet port 102 and cell concentrate outlet port 112, to facilitate flow into and out of ports 102, 112. Such widening of the recirculation flow gap 104 at the upper and lower ends thereof may be accomplished by decreasing the diameter of the rotor 108 at the upper and lower ends thereof so as to result in a widening of the recirculation gap 104 adjacent such region(s) of decreased diameter.

The centrifugation zone 122 is in fluid communication with the recirculation gap 104 through blood inlet ports 132 formed at the base thereof. Such blood inlet ports 132 are preferably positioned at 0.785 inches radius from the central axis of the rotor 108.

Blood outlet ports 134 are formed at spaced intervals around the top end of the rotor 108, and also form fluid passageways between the centrifugation zone 122 and the recirculation gap 104. Such blood outlet ports 134 are preferably spaced at a greater radial distance from the central axis of the rotor 108 then are the blood inlet ports 132. In the preferred embodiment shown, such blood outlet ports 134 are spaced at 0.889 inches radius from the central axis of the rotor 108.

The difference in radial distance of the blood inlet ports 132 and blood outlet ports 134 from the central axis of the rotor 108 result in substantially greater rotational velocity at the outlet ports 134 then at the inlet ports 132, thereby causing a substantial force in the upward direction on blood within the centrifugation zone 122. Blood exiting outlet ports 134 will flow out of cell concentrate port 112 and/or may be recirculated downwardly through recirculation zone 104 to the base of the housing 100 whereat such recirculated blood may, once again, re-enter the centrifugation zone 122 through blood inlet ports 132.

In operation, whole blood is pumped at substantially continuous pressure into blood inlet 102 and a rotating magnetic force is applied to magnetic drive unit 109, thereby causing rotor 108 to rotate at a constant speed, preferably of about 3600 r.p.m. Blood platelets and a portion of the blood plasma will drain inwardly through platelet-rich plasma ports 116 and downwardly through tube 110 so as to exit the housing 100 through the platelet-rich plasma outlet port 130. The remaining blood plasma and cellular constituents ("cell concentrate") passes outwardly through blood outlet ports 134 and either exits the housing through cell concentrate port 112 or is recirculated downwardly through recirculation gap 104 whereat it combines with additional entering whole blood and is again subjected to passage through the centrifugation zone 122.

In normal operation, the cell concentrate exiting the cell concentrate outlet port enters a pooling vessel or container whereat it is mixed with entering whole blood, thereby providing for repeated recirculation of blood through the whole blood separator apparatus 44a until the desired amount of platelet-rich plasma has been extracted from a known volume of blood.

Further and more detailed explanation of the operational variables and functioning of the preferred whole blood separator apparatus 44a is fully described and illustrated in U.S. Pat. No. 4,944,883 (Schoendorfer, et al.) which is expressly incorporated herein by reference.

ii. A Preferred Rotating Membrane Separator Device Useable In Stages 2 and 3 of the Invention The separation of cell free plasma from leukocyte contaminated platelet concentrate and the separation of leukocytes from the platelet concentrate as carried out in Stages 2 and 3 of the present invention may be accomplished by a rotating membrane separator of the type described in U.S. Pat. No. 5,034,135 (Fischel) and available commercially under the name PLASMACELL™ from Baxter Healthcare Corporation, Fenwal Division, Deerfield, Ill.

The entire disclosure, including the drawings, of U.S. Pat. No. 5,034,135 (Fischel) is expressly incorporated herein by reference as if fully set forth, verbatim, in this patent application.

It will be appreciated that, although the same rotating membrane filter device may be utilized in both Stages 2 and 3 of the process of the present invention, the thickness and pore size of the membrane within such device will differ between Stages 2 and 3 of invention as described more fully herebelow.

FIGS. 4a and 4b of this application show the presently preferred rotating membrane separator device 60 useable in Stages 2 and 3 of the process of the present invention. In summary, this preferred rotating membrane separator device 60 comprises an outer cylindrical wall or housing 200 having an inner wall surface 202. A cylindrical rotor or spinner is rotationally mounted within housing 200. The outer surface of spinner 204 is provided with corrugations or scallops 206, as shown. A microporous membrane 208 is mounted on and carried by rotor 204. A space or gap 210 exists between the inner surface 202 of the housing 200 and the outer surface of the microporous membrane 208. In the embodiment shown, the width of gap 210 is in the range 0.020–0.030 and preferably about 0.023 inches, length of gap 210 is preferably 2.5–3.5 and preferably about 3 inches.

Inlet port 212 and outlet port 214 are fluidly communicative with gap 210. In the embodiment shown, the inlet port 212 comprises a tubular member positioned tangentially to the housing 200 near the bottom of the device 60 while the outlet port 214 comprises a tubular member positioned tangentially to the housing 200 near the top portion thereof.

The inlet port 212 and outlet port 214 may be inverted (such that the inlet is at the top and the outlet is at the bottom) without diminishing the efficiency of the filtration provided that the direction of the rotation of rotor 204 is correspondingly changed.

A magnetic drive unit 216 positioned within the top of the rotor 204 causes the rotor 204 to spin when driven by a rotating magnetic field.

Filtrate inlet apertures 222 are formed through the opposite sides of the bottom portion of the rotor 204 and lead into manifold passageways 222. Manifold passageways 222 are fluidly communicative with a central tube 224 whereby filtrate entering apertures 220 may pass inwardly through manifold 222 and drain downwardly through tube 224 and out of filtrate outlet 227.

In operation, the rotor 204 is rotated at a speed of 1500–2000 r.p.m. and preferably about 1600–1800 r.p.m. while the blood fraction to be filtered is infused under constant pressure through inlet 212, filling gap 210. Rotation of the membrane-carrying spinner 204 creates movement of the fluid within gap 210. This movement, which takes the form of vortices, technically known as "Taylor Vortices", induces transport of non-filterable cellular material away from membrane 208 while filterable material or liquid plasma passes through the pores of microporous filter 208, drains downwardly through channels 226, inwardly through apertures 220 and manifolds 222 and subsequently drains out of housing through filtrate outlet 227.

Unfiltered material which exits the housing through outlet port 214 may be subsequently recirculated through inlet 212 so as to provide for repeated passage of such unfiltered material over filter 208, thereby optimizing extraction of the desired filtrate therefrom.

a. Equipping the Preferred Rotating Membrane Separator Device to Carry Out Stage 2 of the Process In Stage 2 of the process of the present invention, it is necessary to extract a quantity of substantially cell free plasma from platelet-rich plasma (PRP) to yield a quantity of leukocyte contaminated platelet concentrate (LCPC).

To perform the desired separation of Stage 2, the microporous filter 208 of the rotating membrane separator device 60 of FIG. 4a comprises a plastic film membrane preferably of nylon, having a thickness of approximately 150 microns and having pores of less than 1.0 micron, and preferably of approximately 0.8 micron, formed therein. Such pore sizes below 1 micron, and preferably approximately 0.8 micron, will filter only cell free liquid plasma therethrough. Leukocytes typically range in size from 5–14 microns and platelets typically range in size from 2–3 microns. Thus, both leukocytes and platelets are typically too large to pass through membrane pores of less than 1 micron. As a result, a portion of the liquid plasma will pass through the 1 micron membrane pores but platelets and leukocytes (along with some remaining plasma) will comprise the unfiltered material and will exit the rotating membrane filter device 60 through the outlet port 214. Repeated passes through the filtration apparatus may be made until a desired platelet concentration (eg. 1.5–1.8 million platelets per microliter of plasma) is contained in the unfiltered residual material.

The cell free plasma filtrate which passes through the microporous membrane 208 will exit the rotating membrane filter device 60 through filtrate outlet 227.

The rotational velocity of the membrane 208 is maintained at a level that induces sheer high enough to maximize separation efficiency but not so high as to damage or activate the platelets. Typically, rotation rates of approximately 1600–1700 r.p.m. are utilized in Stage 2.

Transmembrane pressures may be controlled or optimized by varying the infusion rate of the platelet-rich plasma (PRP) through inlet 212. Infusion rates of approximately 80–120 ml/min are typically useable.

ii. Equipping the Rotating Membrane Filter Device to Carry Out in Stage 3 of the Process In Stage 3 of the process of the present invention, it is necessary to separate leukocytes from the leukocyte contaminated platelet concentrate (LCPC) to yield a desired leukocyte depleted platelet concentrate (LCPC).

To perform the desired separation of Stage 3, the microporous membrane 208 of the rotating membrane filter device 60 of FIG. 4a preferably comprises a plastic film membrane preferably of polycarbonate, having a thickness of 10 microns and having pores of 3.0–3.5 microns, and preferably approximately 3.0 microns, formed therein. Such pore size of 3.0–3.5 micron allows the lighter and smaller platelets, along with the liquid plasma, to pass through the membrane while effectively excluding the larger leukocytes.

Rotational velocity of the membrane 208 is maintained at a level that induces sheer high enough to maximize separation efficiency but not so high as to damage or activate the platelets. Typically, rotation rates of approximately 1600–1700 r.p.m. are utilized in Stage 3.

In the preferred embodiment shown, the actual filtration area of the membrane 208 is approximately 70 sq. cm.

The pore density of the microporous membrane 208 is preferably approximately $2 \times 10^6$ pores/sq. cm. One example of a commercially available polycarbonate membrane having a thickness of approximately 10 microns and having pores of approximately 3 micron size, at a density of $2 \times 10^6$ pores/sq. cm., is that commercially available from Costar-Nucleopore Corp., Pleasanton, Calif.

Transmembrane pressure may be controlled or optimized by varying the infusion rate of the leukocyte contaminated platelet concentrate (LCPC) through inlet 212. Infusion rates of approximately 80 ml/min are typically useable.

C. Preferred Tubing/Component Systems for Preparing LDPC Using Automated Apheresis Instrumentation FIGS. 2a, 2b and 2c show automated apheresis instruments, tubing harnesses and components which are useable to sequentially effect the three stage process of the present invention.

Figure 2A:
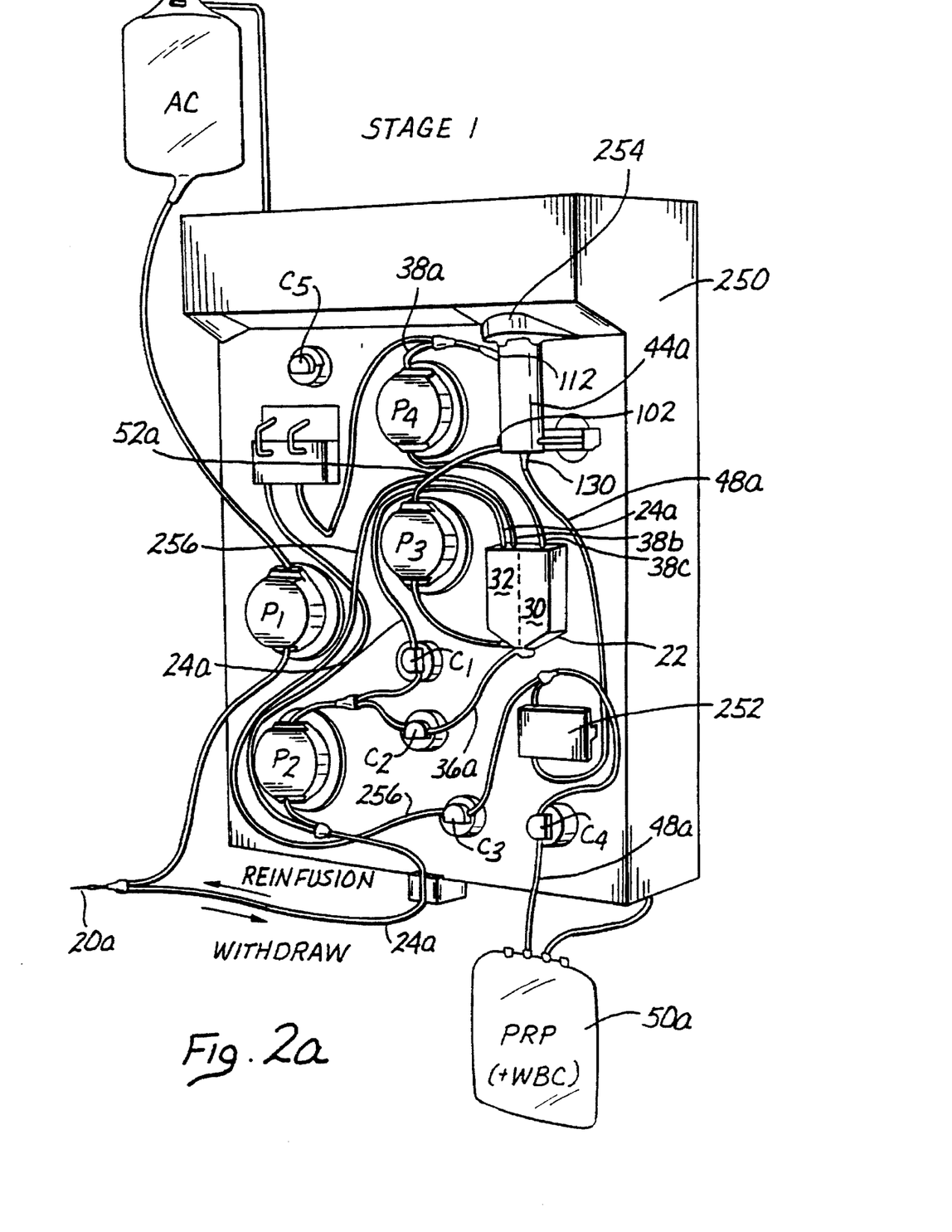
FIG. 2a is a perspective view of an automated apheresis instrument adapted and outfitted to carry out the first stage of a process of the present invention.
Figure 2B:
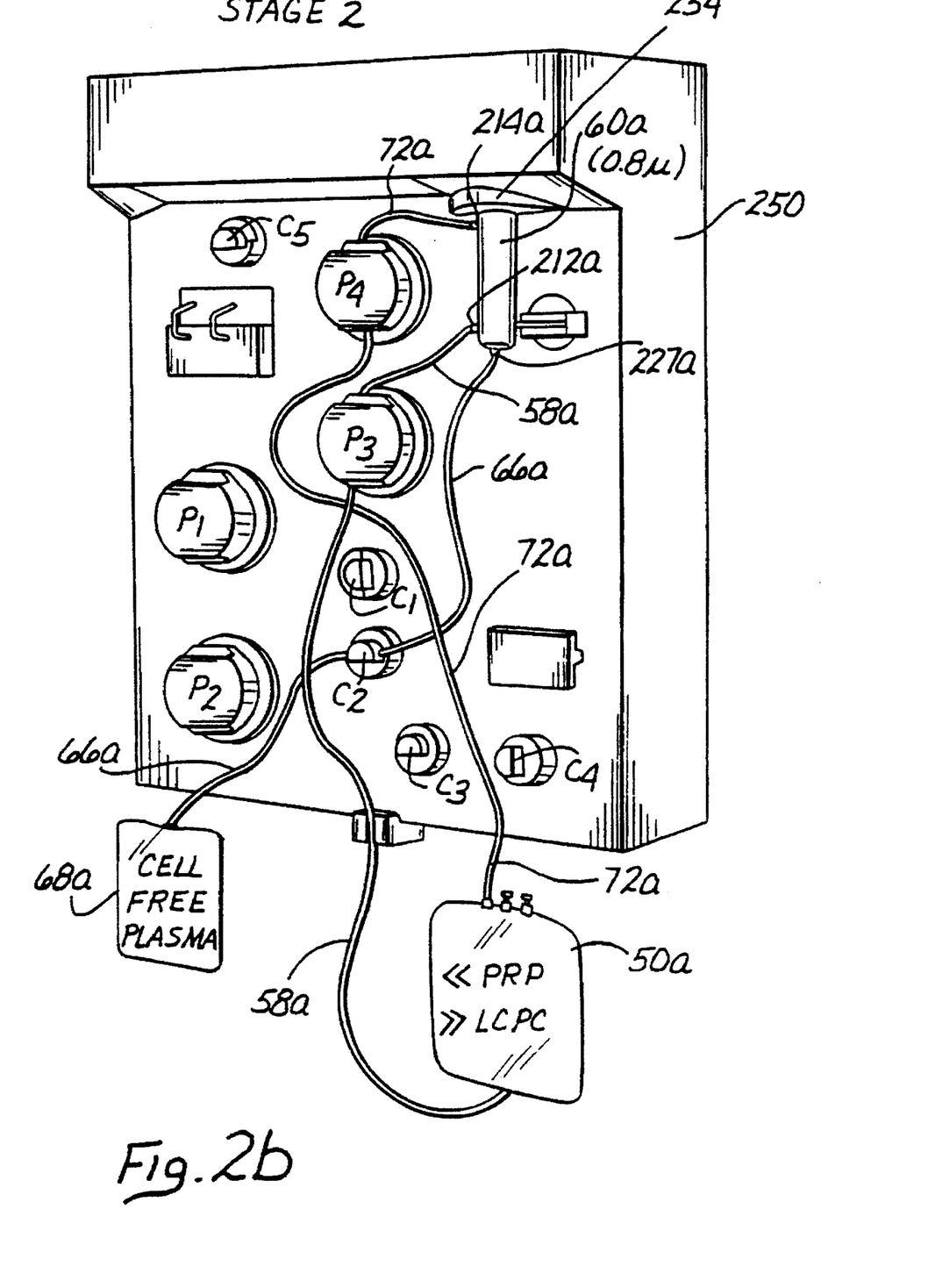
FIG. 2b is a perspective view of an automated apheresis instrument adapted and outfitted to carry out the second stage of a process of the present invention.
Figure 2C:
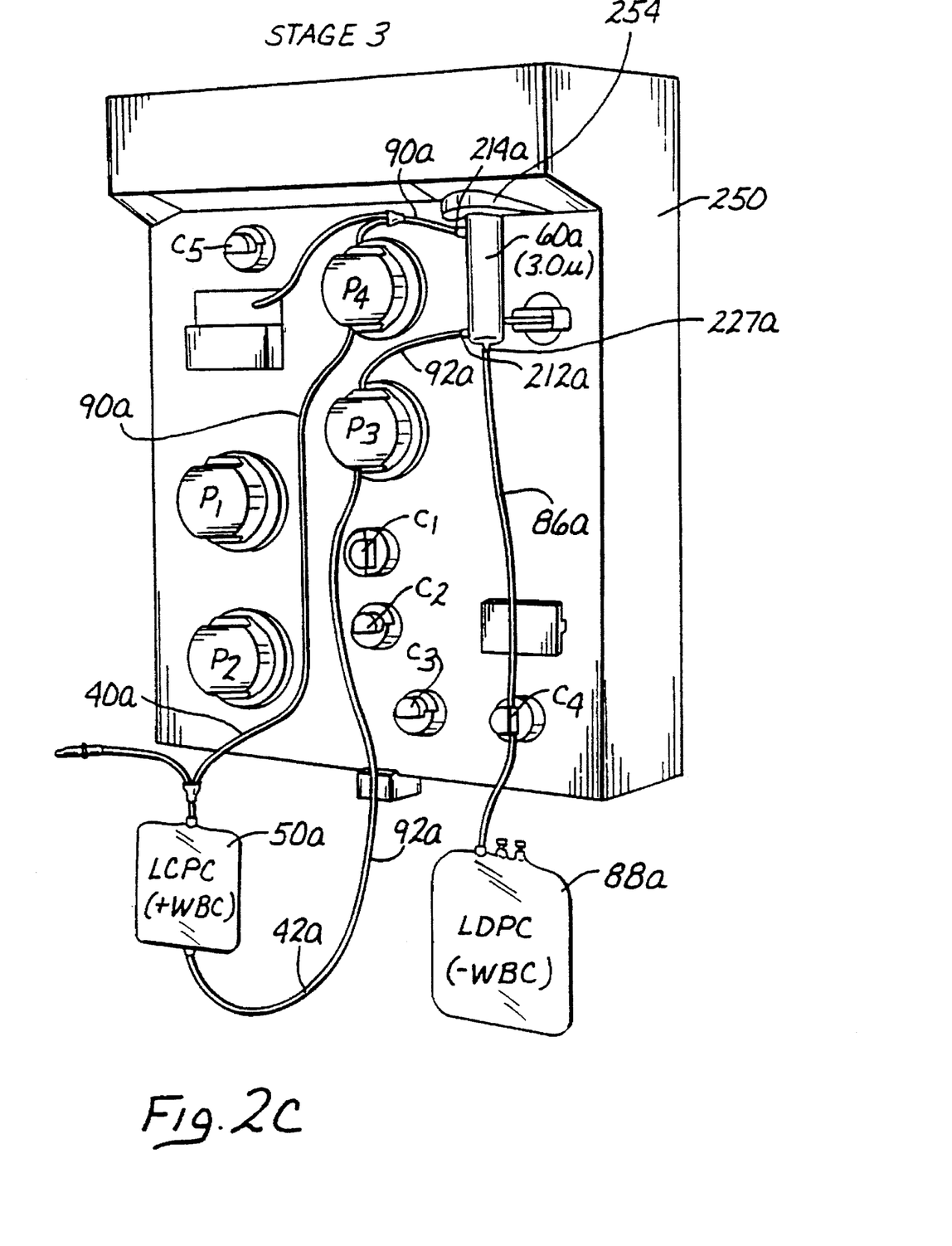
FIG. 2c is a perspective view of an automated apheresis instrument adapted and outfitted to carry out the third stage of a process of the present invention.

The particular apheresis instrument shown in FIGS. 2a–2c comprises a microprocessor controlled instrument of the type available commercially as the AUTOPHERESIS-C® PLASMAPHERESIS SYSTEM, Baxter Healthcare Corporation, Fenwal Division, Deerfield, Ill. 60015.

The apheresis instrument used for Stages 1, 2 and 3 of the process of the present invention comprises a microprocessor controlled, automated system having a housing 250.

The automated apheresis instrument is initially utilized in conjunction with a first tubing/component set. Such first tubing/component set is provided with a single venepuncture needle 20a for alternately receiving whole blood from a donor and reinfusing packed cells into the donor. The venepuncture needle 20a is connected to blood line 24a. Blood line 24a passes through pump P2 and into the left chamber 32 of reservoir 22a. An anticoagulant line 25a is attachable to a bag or container of anticoagulant (AC) at one end and is joined with bloodline 24a at the other end. Anticoagulant line 25a passes through pump P1 such that pump P1 may be utilized to deliver a metered amount of anticoagulant through anticoagulant line 25a into the flow of blood being withdrawn through bloodline 24a.

A second bloodline 38a passes out of an outlet port positioned at the bottom of the left chamber 32 of reservoir 22a, through pump P3 and into the whole blood inlet port 42a of whole blood separator apparatus 44a. Pump P3 is utilized to pump controlled amounts of blood through second bloodline 38a into whole blood separator apparatus 44a.

Whole blood separator apparatus 44a is rotationally driven by the magnetic drive apparatus 254 of the automated apheresis instrument 250.

Platelet-rich plasma (containing leukocytes) exits whole blood separator apparatus 44a through platelet-rich plasma outlet port 46a and passes downwardly through platelet-rich plasma line 48a and through hemoglobin detector 252. If a significant level of hemoglobin is detected as would indicate the presence of undesirable red blood cell contamination, clamp C4 will be closed and clamp C3 will be open, thereby shunting the flow of platelet-rich plasma from line 48a, through return line 256 and once again into the left chamber 32 of reservoir 22a whereat such platelet-rich plasma will be combined with withdrawn whole blood and recirculated through the whole blood separator apparatus 44a to remove such contaminating red blood cells.

If the hemoglobin detector 252 detects substantially no hemoglobin (i.e. less than 5 mg/dl), clamp C3 will be closed, and clamp C4 will be open, thereby allowing the flow of platelet-rich plasma to continue through line 48a and into the platelet-rich plasma container 50a.

Cell concentrate exits the whole blood separation apparatus 44a through cell concentrate outlet port 40a and is pumped by pump P4 through line 53a into the right chamber 30 of reservoir 22a. Upon pooling of an adequate amount of cell concentrate in chamber 30, the instrument 250 will switch a reinfusion cycle, clamp C1 will be closed, clamp C2 will be open and pump P2 will operate to pump cell concentrate from chamber 30, through return line 36a into bloodline 24a and through needle 20a into the vasculature of the patient, thereby accomplishing reinfusion of the unharvested cellular constituents of the blood. The timing of the alternate withdrawal and collection cycles and the overall timing of the platelet-rich plasma collection is controlled by way of sensors (not shown) on the instrument 250 which detect the quantities of fluids in the right and left chambers, 30, 32 of the reservoir 22a and the quantity of platelet-rich plasma collected in the PRP container 50a. Information generated by such sensors is provided to the microprocessor of the instrument 250 wherefrom responsive signals are emanated to cause the instrument to cycle or change from its blood collection cycle to reinfusion cycle in the appropriate manner. It will be appreciated that during the alternate collection and reinfusion cycles, whole blood is continuously pumped from reservoir compartment 32 to whole blood separator apparatus 44a by pump P3, whereby separation is effected continuously. Thus, platelet-rich plasma flows continuously from whole blood separator apparatus 44a although the instrument 250 may simultaneously be cycling between withdrawal and reinfusion cycles.

When the desired quantity of platelet-rich plasma (PRP) has been collected in platelet-rich plasma container 50a, the microprocessor of the instrument 250 will terminate the collection period and will cause the instrument to undergo a purge cycle whereby residual blood and/or blood products are purged from the first tubing/component set disposed on the instrument 250.

After the first tubing/component set has been purged of residual blood and/or blood products, the first tubing/component set is removed from the face of the instrument 250 and a second tubing/component set is applied to the instrument 250 to conduct stage 2 of the process, as shown in FIG. 2b.

With reference to FIG. 2b, the second tubing/component set utilized to conduct Stage 2 of the process is provided with a rotating membrane separator apparatus 60a capable of separating cell free plasma from the platelet-rich plasma collected in Stage 1 of the process, thereby providing a quantity of leukocyte contaminated platelet concentrate for subsequent leukocyte depletion.

Platelet-rich plasma line 58a fluidly connects the platelet-rich plasma container 50a to the inlet port 62a of rotating membrane separator 60a. Pump P3 is utilized to pump a flow of platelet-rich plasma from platelet-rich plasma container 50a through line 58a into the inlet port 62a of rotating membrane separator apparatus 60a. Leukocyte contaminated platelet concentrate (LCPC) exits the rotating membrane separator apparatus 60a through outlet port 70a and is pumped by pump P4 through line 72a back into platelet-rich plasma container 50a, thereby mixing with any remaining platelet-rich plasma in the platelet-rich plasma container 50a.

The substantially cell free plasma filtrate exits the rotating membrane separator apparatus 60a through filtrate outlet port 64a and passes through line 66a into cell free plasma container 68a.

This second stage of the processes is continued until a desired amount of substantially cell free plasma has been collected in cell free plasma container 68a and a corresponding amount of leukocyte contaminated platelet concentrate has replaced the original platelet-rich plasma in container 50a.

When such endpoint has been reached, the instrument 250 will terminate the second stage of the procedure and the second tubing/component set will be removed from the face of the instrument 250 and replaced with a third tubing/component set as shown in FIG. 2c.

The third tubing/component set positioned on the instrument 250 in FIG. 2c includes the preferred rotating membrane separator apparatus 60b of the present invention equipped with a membrane having pores of approximately 3.0 microns such that relatively small platelets will pass through such 3.0 micron pores while the relatively large leukocytes will be excluded by such 3.0 micron pores. The leukocyte contaminated platelet concentrate contained within container 74a is pumped out of the bottom of container 74a, through line 92a, by pump P3 and into the inlet port 82a of rotating membrane filter apparatus 60b. Leukocyte depleted platelet concentrate will exit rotating membrane filter apparatus 60b through filtrate outlet port 84a and will pass through line 86a into leukocyte depleted platelet concentrate container 88a. Leukocyte concentrate will pass out of outlet port 214a of rotating membrane filter apparatus 60b and will be pumped by pump P4 through return line 90a into container 74a where it will mix with any remaining leukocyte contaminated platelet concentrate. Such recirculating process will continue until such time as a desired target amount of leukocyte depleted platelet concentrate has been obtained in container 88a. Thereafter, the instrument 250 will signal a shut-down procedure whereby pumps P3 and P4 will be stopped, and rotation of the rotating membrane filter apparatus 60b will be terminated. Thereafter, the container 88a of leukocyte depleted platelet concentrate may be separated from the third tubing/component set and subjected to standard blood banking procedures in preparation for transfusion of such leukocyte depleted platelet concentrate (LDPC) to a recipient patient.

It will be appreciated that the first, second and third tubing/component sets may be initially interconnected and unitarily packaged such that each of the first, second and third tubing/component sets may be individually deployed and mounted on the face of the instrument 250 while the remaining non-deployed tubing/component sets remain in a collapsed or folded configuration for subsequent use. In such embodiments, after each of the first, second and third tubing/component sets has been deployed and used, such used tubing/component set may be cut off of or otherwise separated from the remaining tubing/component sets, thereby separating the soiled used tubing/component set from the remaining clean unused tubing/component sets.

Additionally, although the invention has been described herein with the second stage of the invention comprising the volume reduction of the leukocyte contaminated platelet-rich plasma to LCPC and the third stage comprising the removal of leukocytes to form the desired LDPC, such second and third stages of the invention may be positionally inverted such that the second stage actually comprises the above-described third stage and the third stage actually comprises the above-described second stage. In such embodiments, the second stage of the invention will effect removal of leukocytes from the leukocyte depleted platelet-rich plasma. Thereafter, the third stage of the invention will effect the reduction in volume of the leukocyte contaminated platelet-rich plasma to form the desired leukocyte depleted platelet concentrate.

It will be appreciated that the invention has been described herein with reference to certain presently preferred embodiments of the invention. The detailed description and drawings setting forth these presently preferred embodiments of the invention are not intended to describe or show the only means by which the present invention may be effected. In fact, numerous other embodiments and devices for effecting the invention will be apparent to those skilled in the art upon reading and understanding of the description set forth in this patent application. Accordingly, it is intended that all such other embodiments and devices for the effecting the invention be included within the scope of the following claims and/or the equivalents thereof.

What is claimed is:

1. A tubing harness/component system which is usable in conjunction with an automated apheresis device to isolate leukocyte depleted platelet concentrate from whole blood, said system comprising:
   a) a first tubing harness/component set comprising:
      i) a reservoir having first and second containment chambers formed therein;
      ii) a separator apparatus for separating platelet rich plasma from whole blood comprising a housing having a separator mounted therein, said housing having a whole blood inlet port, a platelet rich plasma outlet port and a cell concentrate outlet port, formed therein;
      iii) a platelet rich plasma container having an inlet port and an outlet port formed therein;
      iv) a first blood tube having a distal end which is attachable to a venipuncture needle and a proximal end connected to the first chamber of said reservoir such that blood may be drawn through the venipuncture needle, through said first blood tube, and into said first chamber of said reservoir;
      v) a second blood tube extending from the first chamber of said reservoir to the whole blood inlet of said separator apparatus such that blood which collects in the first chamber of said reservoir may pass through said second blood tube and into said whole blood separator apparatus;
      vi) a cell concentrate tube extending from the cell concentrate outlet port of said separator apparatus to the second chamber of said reservoir such that cell concentrate may pass from said separator apparatus into the second chamber of said reservoir;
      vii) a second cell concentrate tube extending from the second chamber of said reservoir to said first blood tube such that cell concentrate which collects in the second chamber of said reservoir may be pumped through said second cell concentrate tube and into said first blood tube so as to be reinfused through said venipuncture needle; and
      viii) a platelet rich plasma tube extending from the platelet rich plasma outlet port of said separator apparatus to the inlet port of said platelet rich plasma container such that platelet rich plasma may pass from said separator apparatus, through said platelet rich plasma tube, and into said platelet rich plasma container;
   b) a second tubing harness/component set comprising:
      i) a second separator apparatus for separating leukocyte contaminated platelet concentrate from platelet rich plasma which has collected in said platelet rich plasma connector, said second separator apparatus comprising a housing having a separator positioned therein, said housing having a platelet rich plasma inlet port, a leukocyte contaminated platelet concentrate outlet port, and a cell free plasma outlet port formed therein;
      ii) a leukocyte contaminated platelet concentrate container having an inlet port and an outlet port formed therein;
      iii) a cell free plasma container having an inlet port formed therein;
      iv) a platelet rich plasma tube extending from the outlet port of said platelet rich plasma container to the inlet port of said second separator apparatus such that platelet rich plasma may flow from said platelet rich plasma container, through said platelet rich plasma tube, and into said second separator apparatus;
      v) a leukocyte contaminated platelet concentrate tube extending from the leukocyte contaminated platelet concentrate outlet port of said second separator apparatus to the inlet port of said leukocyte contaminated platelet concentrate container; and
      vi) a cell-free plasma tube extending from the cell free plasma outlet port of said second separator apparatus to the inlet port of said cell free plasma container; and,
   c) a third tubing harness/component set comprising:
      i) a third separator apparatus for separating leukocyte depleted platelet concentrate from leukocyte contaminated platelet concentrate which has collected in said leukocyte contaminated platelet concentrate container, said third separator comprising a housing having a separator mounted therein, said housing having a leukocyte contaminated platelet concentrate inlet port, a leukocyte depleted platelet concentrate outlet port, and a leukocyte concentrate outlet port formed therein;
      ii) a leukocyte contaminated platelet concentrate tube extending from the outlet port of said leukocyte contaminated platelet concentrate container to the inlet port of said third separator apparatus such that leukocyte contaminated platelet concentrate may flow from said leukocyte contaminated platelet concentrate container into said third separator apparatus; and,
      iii) a leukocyte depleted platelet concentrate tube extending from a leukocyte depleted platelet concentrate outlet port of said third separator apparatus to the inlet port of said leukocyte depleted platelet concentrate container to carry leukocyte depleted platelet concentrate from said third separator apparatus to said leukocyte depleted platelet concentrate container.

2. The system of claim 1 wherein said separator apparatus comprises:
   a rigid outer housing;
   a centrifugal rotor rotatably mounted within said housing to centrifugally separate whole blood into a platelet rich plasma fraction and a cell concentrate fraction.

3. The system of claim 1 wherein said second separator apparatus comprises:

a rigid outer housing;

a microporous filter rotatably mounted within said housing, said microporous filter having pores of less than 1 micron in size;

said microporous filter being operative to separate liquid plasma which passes through said pores of less than 1 micron from platelets, leukocytes and residual liquid plasma which do not pass through said pores of less than 1 micron.

4. The system of claim 3 wherein the pores of said microporous filter are approximately 0.8 microns in size.

5. The system of claim 3 wherein said microporous filter of said second separator apparatus is rotatable within said housing at approximately 1600–1700 revolutions per minute.

6. The system of claim 1 wherein said third separator apparatus comprises:

a rigid outer housing;

a microporous filter rotatably mounted within said rigid outer housing, said microporous filter having pores of 3.0–3.5 microns in size;

said microporous filter being operative to separate platelet rich plasma which passes through said 3.0–3.5 micron pores, from leukocytes and residual plasma which do not pass through said 3.0–3.5 micron pores.

7. The system of claim 6 wherein the microporous filter of said third separator apparatus is rotatable within said housing at approximately 1600–1800 revolutions per minute.

8. A tubing harness/component system which is usable in conjunction with an automated apheresis device to isolate leukocyte depleted platelet concentrate from platelet rich plasma, said system comprising:

a) an initial tubing harness/component set comprising:

i) an initial separator apparatus for separating leukocyte contaminated platelet concentrate from platelet rich plasma which has collected in said platelet rich plasma connector, said initial separator apparatus comprising a housing having a separator positioned therein, said housing having a platelet rich plasma inlet port, a leukocyte contaminated platelet concentrate outlet port, and a cell free plasma outlet port formed therein;

ii) a leukocyte contaminated platelet concentrate container having an inlet port and an outlet port formed therein;

iii) a cell free plasma container having an inlet port formed therein;

iv) a platelet rich plasma tube extending from the outlet port of said platelet rich plasma container to the inlet port of said initial separator apparatus such that platelet rich plasma may flow from said platelet rich plasma container, through said platelet rich plasma tube, and into said initial separator apparatus;

v) a leukocyte contaminated platelet concentrate tube extending from the leukocyte contaminated platelet concentrate outlet port of said initial separator apparatus to the inlet port of said leukocyte contaminated platelet concentrate container; and vi) a cell-free plasma tube extending from the cell free plasma outlet port of said initial separator apparatus to the inlet port of said cell free plasma container; and, b) a secondary tubing harness/component set comprising:

i) a secondary separator apparatus for separating leukocyte depleted platelet concentrate from leukocyte contaminated platelet concentrate which has collected in said leukocyte contaminated platelet concentrate container, said secondary separator apparatus comprising a housing having a separator mounted therein, said housing having a leukocyte contaminated platelet concentrate inlet port, a leukocyte depleted platelet concentrate outlet port, and a leukocyte concentrate outlet port formed therein;

ii) a leukocyte contaminated platelet concentrate tube extending from the outlet port of said leukocyte contaminated platelet concentrate container to the inlet port of said secondary separator apparatus such that leukocyte contaminated platelet concentrate may flow from said leukocyte contaminated platelet concentrate container into said secondary separator apparatus; and, iii) a leukocyte depleted platelet concentrate tube extending from a leukocyte depleted platelet concentrate outlet port of said secondary separator apparatus to the inlet port of said leukocyte depleted platelet concentrate container to carry leukocyte depleted platelet concentrate from said secondary separator apparatus to said leukocyte depleted platelet concentrate container.

9. The system of claim 8 wherein said initial separator apparatus comprises:

a rigid outer housing;

a microporous filter rotatably mounted within said housing, said microporous filter having pores of less than 1 micron in size;

said microporous filter being operative to separate liquid plasma which passes through said pores of less than 1 micron, from platelets, leukocytes and residual liquid plasma which do not pass through said pores of less than 1 micron.

10. The system of claim 8 wherein said pores are approximately 0.8 microns in size.

11. The system of claim 8 wherein said microporous filter is rotatable at approximately 1600–1800 revolutions per minute RPMs.

12. The system of claim 8 wherein said secondary separator apparatus comprises:

a rigid outer housing;

a microporous filter rotatably mounted within said rigid outer housing, said microporous filter having pores of 3.0–3.5 microns in size;

said microporous filter being operative to separate platelet rich plasma which passes through said 3.0–3.5 micron pores, from leukocytes and residual plasma which do not pass through said 3.0–3.5 micron pores.

13. The system of claim 12 wherein the microporous filter of said secondary separator apparatus is rotatable within said housing at approximately 1600–1800 revolutions per minute.

* * * * *